United States Patent
Minghetti et al.

(10) Patent No.: US 6,544,965 B2
(45) Date of Patent: Apr. 8, 2003

(54) COMPOUNDS WITH AN ANTIOXIDANT ACTIVITY, COMPOSITIONS USEFUL AS FOOD INTEGRATORS CONTAINING THEM AND PROCESS FOR THEIR PREPARATION

(75) Inventors: Anacleto Minghetti, Milan (IT); Nicoletta Crespi Perellino, Milan (IT); Aldo Roda, Bologna (IT); Bruno Danieli, Milan (IT); Giuliano Frigerio, Arese (IT); Danila Ingrid Marchioretto, Sesto San Giovanni (IT)

(73) Assignee: Giuliani S.p.A., Milan (IT)

( * ) Notice: Subject to any disclaimer, the term of this patent is extended or adjusted under 35 U.S.C. 154(b) by 77 days.

(21) Appl. No.: 09/760,204

(22) Filed: Jan. 12, 2001

(65) Prior Publication Data

US 2001/0024809 A1 Sep. 27, 2001

(30) Foreign Application Priority Data

Jan. 20, 2000 (IT) .......................... MI00A0066

(51) Int. Cl.[7] ...................... A61K 31/715; A61K 31/70; C07H 15/04; C12P 19/00; C12P 19/44
(52) U.S. Cl. ............................ 514/61; 514/25; 536/4.1; 536/116; 536/128; 435/72; 435/74
(58) Field of Search ................... 514/61, 25; 536/4.1, 536/128, 116; 435/72, 74

(56) References Cited

FOREIGN PATENT DOCUMENTS

EP  0 466 375 A  1/1992

(List continued on next page.)

OTHER PUBLICATIONS

Gao et al, "Radical Scavenging Activity of Phenylpropanoid Glycosides in Caryopteris incana", Biosci. Biotechnol. Biochem., vol. 63, No. 6, issued 1999, pp. 983–988.*

(List continued on next page.)

Primary Examiner—James O. Wilson
Assistant Examiner—Everett White
(74) Attorney, Agent, or Firm—Hedman & Costigan, P.C.

(57) ABSTRACT

The present invention relates to the use of a compound having general formula (I) as described hereunder

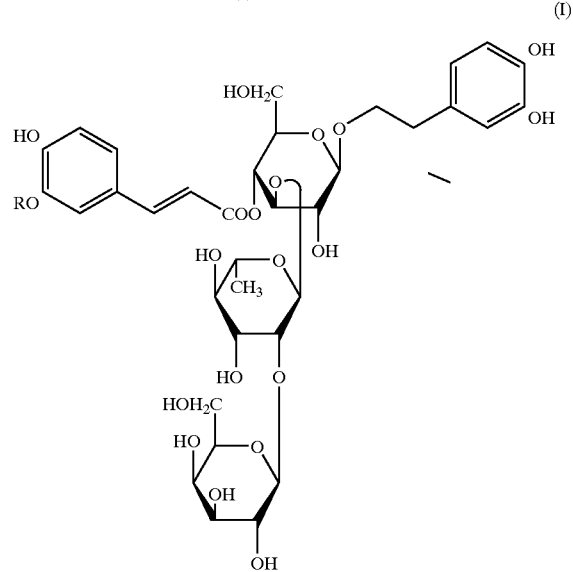

wherein R=H (FPA compound) or R=CH$_3$ (FPB compound) for the preparation of compositions with an antioxidant activity for administering to human beings for therapeutic or nutritional purposes. The invention also relates to a process for the preparation of a compound having general formula (I) as defined above characterized in that a cellular culture is obtained from an *Ajuga reptans* plant, said culture being subsequently subjected to cultivation under aerobic conditions, in a liquid medium containing assimilable carbon and nitrogen sources, and mineral salts.

5 Claims, 2 Drawing Sheets

FOREIGN PATENT DOCUMENTS

Figure 1:
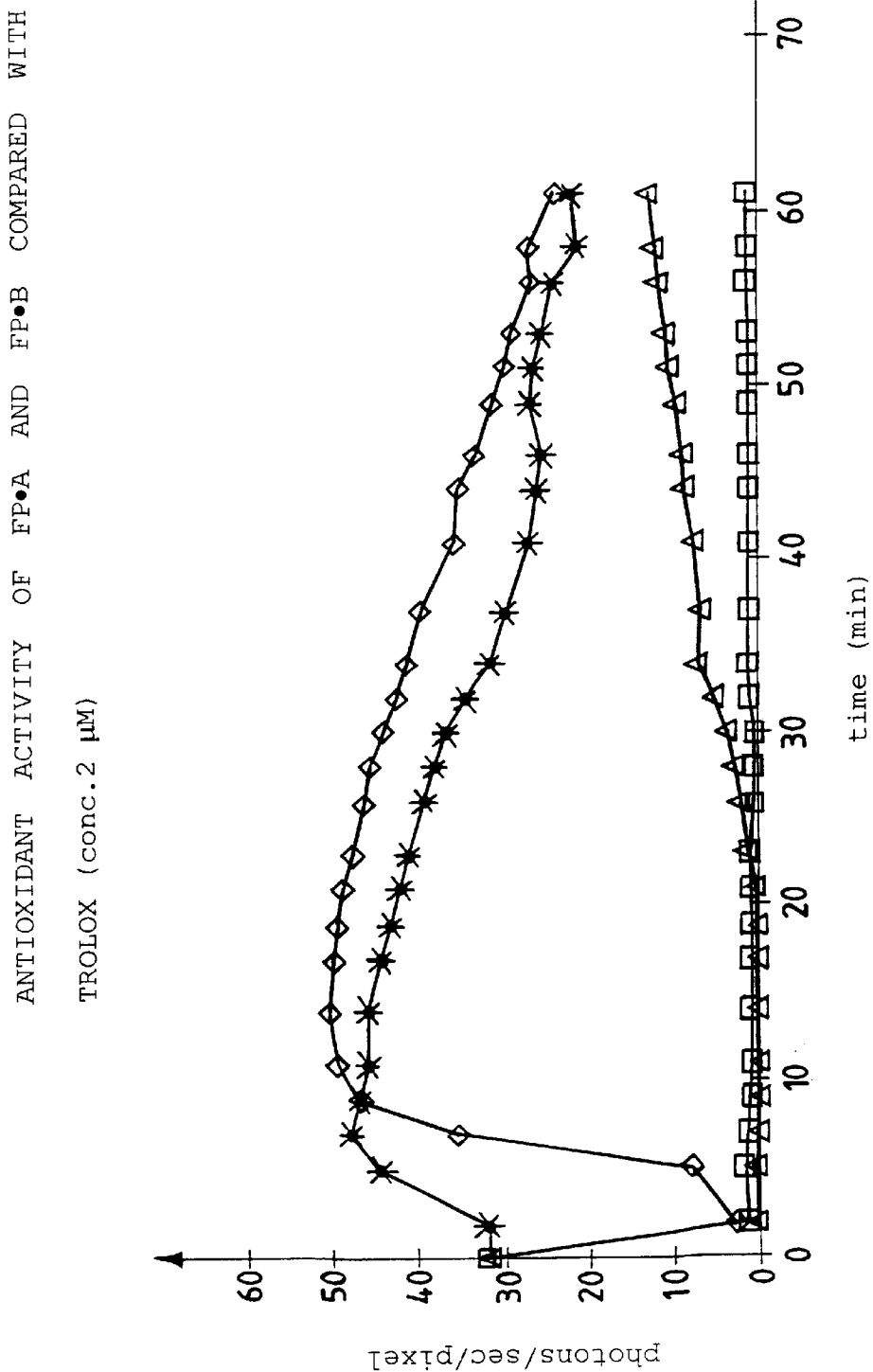

| | | |
|---|---|---|
| EP | 0 471 081 A | 2/1992 |
| WO | WO 92/16544 A | 1/1992 |
| WO | WO 99/45919 A | 9/1999 |

OTHER PUBLICATIONS

Chemical Abstarct, vol. 117, No. 17, Oct. 26, 1992 Columbus, Ohio, US; Oganesyan, G.B. et al.: "Phenylpropanoid glycosides of Teucrium polium" p. 428; col. r; *abstract* & KHIM. PRIR. SOEDIN., 1991, pp. 630–634 XP002166801.

Malakov, P.Y. and Papanov, G.Y.: "Areptins A and B two new neo–clerodane diterpenoids from ajuga reptans" PHYTOCHEM., vol. 49, No. 8, 1998, pp. 2443–2447. XP000986295.

Terahara, N. et al.: "Triacylated anthocyanins from ajuga retans flowers and cell cultures" PHYTOCHEM., vol. 42, No. 1, 1996, pp. 199–203. XP000986294.

Calcagno, M.P. et al.: "New phytoecdysteroids from roots of ajuga retans varieties" TETRAHEDRON vol. 52, No. 30, 1996 pp. 10137–10146, XP004104054.

* cited by examiner

ANTIOXIDANT ACTIVITY OF SERUMS OF RATS TREATED WITH RAW EXTRACT OF AJUGA REPTANS WITH RESPECT TO A NON-TREATED CONTROL

COMPOUNDS WITH AN ANTIOXIDANT ACTIVITY, COMPOSITIONS USEFUL AS FOOD INTEGRATORS CONTAINING THEM AND PROCESS FOR THEIR PREPARATION

The present invention relates to compounds having the formula

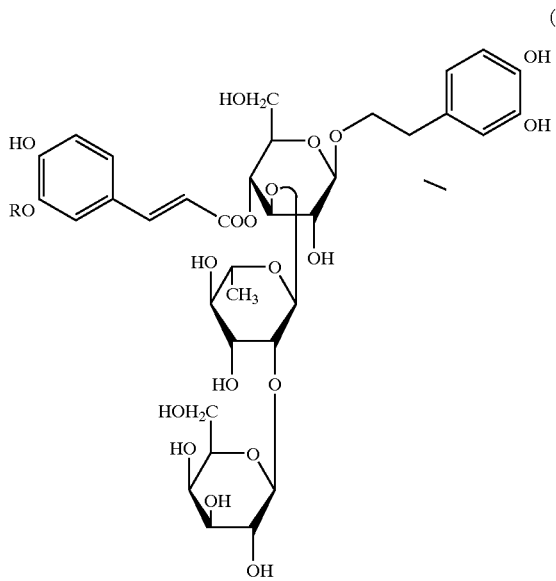

(I)

wherein R can be H or $CH_3$.

Hereinafter in the present description, compound (I) wherein R=H is called FPA.

Compound (I) wherein R=$CH_3$, is called FPB.

FPA (phenylpropanoid glucoside) has been previously described and called teupolioside (Chem. Nat. Compd. 1991, 27:5 556–559), as secondary metabolite, having an antimicrobial activity, present in the plant *Teucrium polium*. The presence of FPA however has never been described in other different plants or in "in vitro" cell cultures of any plant.

FPB, on the other hand, is a compound which has never been described in literature and as such is therefore an object of the present invention. According to a first aspect of the present invention, a production process of FPA and FPB compounds (jointly called FPs, or raw FPs), is proposed.

This consists in cultivating cells of a cellular line taken from a plant of *Ajuga reptans*. For this vegetable species, bibliographical reference can be made to Cantino-Sanders, Syst. Bot. Vol. 11 (1986), pages 163–185.

According to the invention, parts of this plant (leaves, shoots and roots) are sterilized by means of sequential washings with ethanol at 70% for 5 minutes, sodium hypochlorite at 2% for two minutes and mercuric chloride at 0.2% for 45 seconds. After each washing with the sterilizing agents, the parts treated are rinsed with sterile distilled water.

The leaves, shoots and roots are cut into portions, sterilely planted in Gamborg B5 medium [O. L. Gamborg et al. Exp. Cell. Res. 50, (1968), page 151] containing 1 mg/L of naphthalene-acetic acid, 1 mg/L of kinetin, 0.2 g/L of 2, 4-dichlorophenoxyacetic acid (G5 medium) and 7 g/L of agar and are kept in the dark at 28° C.

After 10–15 days an undifferentiated tissue (callus) develops which, after a further 20–30 days, is transferred onto agarized slants of the same medium. 20 days at 28° C. in the dark are normally required for obtaining well grown cultures. After 2 or 3 transfers, stabilized cultures are obtained which are used as inoculum for cultures in suspension.

The cultures grown on solid medium (undifferentiated callus cultures) consist of small masses of colorless and easily disagreeable cells. The elliptic-spherical shaped cells have a diameter of 50–100 μm. Under the above conditions, the calluses undergoing cultivation do not show any signs of organogenesis or any differentiation process. When exposed to light with an intensity equal to at least 2000 lux, the calluses become green due to the biosynthesis of the chlorophyll. Exposure to light, however, does not influence the biosynthesis of the phenylpropanoids.

When cultivated in liquid mediums, the undifferentiated callus cultures of *Ajuga reptans* grow in small aggregates made up of 5–50 cells. The cells have the same shape and size as those grown on solid mediums.

About 1–2 grams of callus (fresh weight) can therefore be transferred to a 300 ml Erlenmeyer flask containing 50 ml of liquid G5 medium. After 28 days of incubation at 28° C. in the dark on a trolley with orbital stirring rotating at 120 revs/minute, the dry weight of the culture is about 15 mg/mL, and 5 mL of vegetative culture are inoculated into Erlenmeyer flasks each containing 50 mL of liquid G5 medium. These cultures are incubated at 23° C. in the dark on a trolley with orbital stirring at 120 revs/minute for 10–14 days.

According to the process of the present invention, the cells are cultivated in a liquid medium. Flasks or fermenters made of glass or other materials generally used, such as, for example, stainless steel, can be adopted. The liquid medium can be a nutritive solution containing an assimilable carbon source, an assimilable source of organic or inorganic nitrogen, inorganic salts and, optionally vegetable hormones and/or vitamins. The assimilable carbon source may consist of carbohydrates such as sucrose, fructose, glucose, starch, dextrin, glycerol, mannitol and mannose.

The assimilable source of organic or inorganic nitrogen can consist of aminoacids or their mixtures, peptides or proteins or their hydrolyzate, casein hydrolyzate, a hydrosoluble fraction of cereals such as the distillation residue of maize or wheat in the production of alcohol, or yeast and also inorganic nitrates and inorganic ammonium salts.

The process of the invention is typically carried out in a culture in suspension, for example in a flask under stirring or in an aerated fermenter with a pH ranging from 5 to 7, preferably 6.5 and at temperatures ranging from 18 to 36° C., preferably 23° C.

The best culture conditions are generally in the dark at a pH of 5.5 to 6.5 and at temperatures ranging from 18 to 32° C., for a duration of 8 to 16 days. The production of raw FPs begins after 2–3 days of growth and reaches its maximum after 10–14 days.

The extraction of the raw FPs can be effected starting either from cells or from the culture medium or from the culture in toto.

The raw FPs are extracted from the filtered cells or from the culture in toto with a solvent miscible with water, such as methanol, ethanol or acetone. The raw FPs are extracted from the culture medium separated from the cells, by means of extraction in solid phase.

The purpose of the following examples is to illustrate the invention, without limiting its scope.

EXAMPLE 1

The process is carried out in 300 mL Erlenmeyer flasks containing 50 mL of G5 medium whose pH is brought to 6.5 with diluted KOH. The flasks were stirred in a rotating stirrer at 120 revs/minute with an eccentric of 4 cm. The optimum incubation temperature was 28° C. The flasks were inoculated with cells of a cellular line of Ajuga reptans, abbreviated CM75, 14 days old, grown on solid G5 medium. After 7 days, 5 mL of the cultures were sterilely transferred to flasks containing 50 ml of the same medium. After a further 14 days, the production of raw FPs determined in HPLC, was 2.2 g/L.

An equal volume of methanol was added to 5 L of cell cultures in suspension obtained from 100 flasks, which were then homogenized and centrifuged.

The sediment was resuspended in 1 L of water and 2 L of methanol and re-extracted twice. The supernatants were joined and concentrated at reduced pressure to 5 L, and the aqueous suspension was passed on an XAD resin column. After washing with 3 L of water and 2 L of methanol at 20%, the material adsorbed was eluted with 3 L of methanol.

The organic solvent containing 10.8 g of raw FPs, determined by HPLC, was evaporated at reduced pressure. The residue was diluted with water and charged onto a column in inverse phase of $C_{18}$ resin.

Elution with acetonitrile at 10% in water gave 7.1 g of FPA and further elution with acetonitrile at 20% gave 2.2 g of FPB, both determined in HPLC. The organic solvent was evaporated at reduced pressure and the aqueous residues of both products were lyophilized giving 7.9 g of FPA and 2.5 g of FPB.

The phenylpropanoid FPA was finally purified by means of chromatography on an RP18 Lobar pre-packed column, eluted with water and increasing quantities of ethanol. The fractions containing pure FPA were joined and lyophilized giving 6.6 g of pure FPA with a titer of over 98%. The phenylpropanoid FPB was purified analogously giving a yield of 1.9 g of pure product with a titer of over 98%.

EXAMPLE 2

10 g of undifferentiated callus of Ajuga reptans grown on solid G5 medium were inoculated into a 2 L flask containing 50 mL of liquid G5 medium. The flask was incubated in an orbital stirrer at 120 revs/minute at a temperature of 28° C. After 7 days, the whole culture was inoculated into a 10 L fermenter containing 6 L of the same medium sterilized at 120° C. for 30 minutes.

The culture in suspension was left to grow for 10 days at 20° C. under stirring at 100 revs/minute and aerated with a stream of air of 0.7 L/L of medium/minute. When the growth had reached a dry weight of about 15 g/L, the culture was collected and extracted as described in example 1.

The yield to FPA corresponded to 1.15 g/L of culture and to 0.36 g/L of FPB.

With respect to the process of the invention, it can generally be seen that the high production yield, the simplicity of the process, which can be effected in normal industrial fermenters, and the fact that structures of phenylpropanoids A and B are almost exclusively produced, form the main advantages of the present invention.

An additional aspect of the present invention consists in the identification of an antioxidant activity for FPA and FPB compounds.

In particular, the antioxidant activity of FPA and FPB compounds extracted from Ajuga reptans according to the process defined above, was tested.

The antioxidant capacity "in vitro" of FPA and FPB compounds, extracted from Ajuga reptans, and "in vitro" of the serum of rats treated with these substances, was evaluated by means of a chemiluminescent method and compared with that of an analogous hydrosoluble product of vitamin E.

The chemiluminescent reaction of luminol was used, which is oxidized by hydrogen peroxide ($H_2O_2$), generating unstable radicals which degenerate to their basic state emitting light. This reaction is catalyzed by peroxidase enzyme. A signal potentiator is also present in the system: p-iodophenol which increases the light emission, producing in turn radicals which degenerate emitting photons.

The presence of substances with an antioxidant activity interrupts the chain of radicalic reactions, temporarily preventing light emission. The time and extinguishing degree of the emission of photons are in relation to the antioxidant capacity and concentration of the substances being tested.

Reagents

ECL reagent (luminol/$H_2O_2$/p-iodophenol) of Amersham International (Amersham, UK).

Radish peroxidase (type VI-A, 1100 U/mg) of Sigma (St. Louis, Mo., U.S.A.).

Trolox: (+/−)-6-hydroxy-2,5,7,8-tetramethylchroman-2-carbonsaeure Sigma (St. Louis, Mo., U.S.A.).

Samples

Samples relating to FPA and FPB molecules extracted from Ajuga reptans, were prepared in aqueous solution at different concentrations (5.0, 2.0, 1.0 and 0.5 µM) and compared with solutions, at equal concentrations, of Trolox, an analogous hydrosoluble product of tocopherol. The serum of rats treated with raw extract of Ajuga reptans by intravenous administration at a dosage of 200 mg/kg were diluted 1:20 with water and compared with the serum of a non-treated rat.

Distilled water was used as control.

Evaluation of the Antioxidant Capacity

The dosage was effected in black polystyrene cylinders (Dynatech Laboratories, Chantilly, Va., U.S.A.). The chemiluminescent mixture was prepared by adding 100 µl of a dilution 1:10,000 v/v (0.11 U/ml) of a stock solution of peroxidase (1 mg/ml in a Tris-HCl 0.1 M buffer, pH 8.6) to 5 ml of ECL reagent. The various dilutions of the samples were distributed in quadruple into the cylinders (50 µL/cylinder) and 100 µl of chemiluminescent mixture were added to each. The light emission was measured immediately using a Luminograph LB980 (EG&G Berthold, Bad Wildbad, Germany) and the chemiluminescent reaction kinetics was monitored for about 60 minutes. The light emission was measured in photons/sec/pixel and the data obtained are indicated in Table 1 and the graph of FIG. 1 enclosed, compared with the control (water) and references (Trolox or serum of a non-treated rat).

TABLE 1

| Time | ECL | Trolox | FPA | FPB |
|---|---|---|---|---|
| 0 | 31.8 | 31.8 | 31.8 | 31.8 |
| 2 | 31.8 | 2.9 | 1.3 | 0.3 |
| 5 | 44.5 | 7.8 | 1.4 | 0.2 |
| 7 | 48 | 35.5 | 1 | 0 |
| 9 | 46.7 | 46.9 | 0.9 | 0 |
| 11 | 45.8 | 49.3 | 0.8 | 0 |
| 14 | 45.5 | 50.4 | 0.8 | 0 |
| 17 | 44.1 | 49.7 | 0.7 | 0 |
| 19 | 43.1 | 49.2 | 0.6 | 0.1 |
| 21 | 41.9 | 48.3 | 0.6 | 0.4 |
| 23 | 40.8 | 47.3 | 0.6 | 1.1 |
| 26 | 38.9 | 46.2 | 0.5 | 1.8 |
| 28 | 37.8 | 45.1 | 0.6 | 2.6 |

TABLE 1-continued

| Time | ECL | Trolox | FPA | FPB |
|---|---|---|---|---|
| 30 | 36.5 | 43.7 | 0.5 | 3.5 |
| 32 | 34.1 | 42.1 | 0.6 | 5.1 |
| 34 | 31.5 | 40.8 | 1.1 | 7 |
| 37 | 29.6 | 39.3 | 0.8 | 6.6 |
| 41 | 26.7 | 35.3 | 0.7 | 7.6 |
| 44 | 25.9 | 35 | 0.9 | 8.6 |
| 46 | 25.1 | 32.8 | 0.8 | 8.9 |
| 49 | 26.8 | 31.1 | 0.8 | 9.6 |
| 51 | 26.1 | 29.6 | 0.8 | 10.3 |
| 53 | 24.9 | 28.6 | 0.8 | 10.9 |
| 56 | 23.8 | 26.2 | 1.1 | 11.4 |
| 58 | 20.7 | 26.8 | 0.8 | 12.1 |
| 61 | 21.9 | 23.9 | 1.1 | 12.7 |

The FPA and FPB samples proved to have an extremely high antioxidant activity in vitro, significantly higher than that of Trolox. The extinguishing time of the light emission with the same concentration is, in fact, much higher, as can be seen from the enclosed graph which indicates the chemiluminescent test kinetics. It can also be observed that the FPA compound has a slightly higher activity with respect to the FPB compound. Table A below shows the antioxidant activity of the compounds under examination and of Trolox, expressed as time in minutes necessary for obtaining a photon emission equal to 50% of the water control.

TABLE A

Time (min.) necessary for reaching 50% of the control light emission

| Concentration | Trolox | FPA | FPB |
|---|---|---|---|
| 5 μM | 15 | >60 | >60 |
| 2 μM | 6 | >60 | >60 |
| 1 μM | 3 | 35 | 29 |
| 0.5 μM | 1 | 13 | 6 |

It can be observed for example that with a dosage of 1 μM the FPA activity is almost 12 times higher than that of Trolox.

Figure 2:
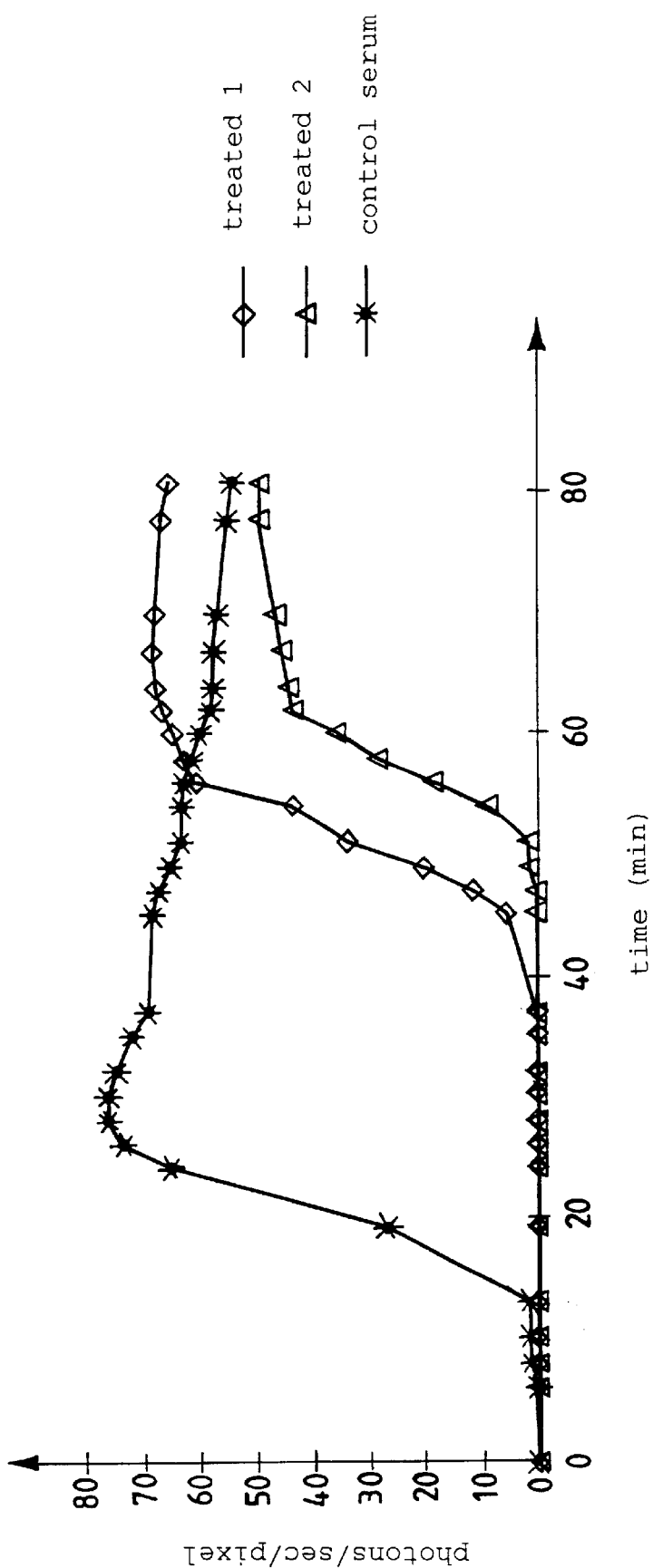

The antioxidant activity "in vivo" was evaluated by the intravenous administration of a raw extract of *Ajuga reptans* at a dosage of 200 mg/kg. The serum of rats treated showed a higher antioxidant activity with respect to the serum of control rats, as can be observed from the following Table 2, and from the corresponding graph of FIG. 2 enclosed.

TABLE 2

| Time | Treated 1 | Treated 2 | Control serum |
|---|---|---|---|
| 0 | 0 | 0 | 0 |
| 6 | 0 | 0 | 0 |
| 8 | 0 | 0 | 1 |
| 10 | 0 | 0 | 1 |
| 13 | 0 | 0 | 1 |
| 19 | 0 | 0 | 26 |
| 24 | 0 | 0 | 65 |
| 26 | 0 | 0 | 73 |
| 28 | 0 | 0 | 76 |

TABLE 2-continued

| Time | Treated 1 | Treated 2 | Control serum |
|---|---|---|---|
| 30 | 0 | 0 | 76 |
| 32 | 0 | 0 | 74 |
| 35 | 0 | 0 | 72 |
| 37 | 0 | 0 | 69 |
| 45 | 5 | 0 | 68 |
| 47 | 11 | 0 | 67 |
| 49 | 20 | 1 | 65 |
| 51 | 33 | 1 | 63 |
| 54 | 43 | 9 | 63 |
| 56 | 60 | 18 | 62 |
| 58 | 62 | 28 | 61 |
| 60 | 64 | 35 | 60 |
| 62 | 66 | 43 | 58 |
| 64 | 67 | 44 | 57 |
| 67 | 68 | 45 | 57 |
| 70 | 67 | 46 | 56 |
| 78 | 66 | 49 | 55 |
| 81 | 65 | 49 | 54 |

In conclusion, these derivatives, and in particular FPA, have proved to have a surprising antioxidant activity both in vitro and in vivo, much higher than that of the strongest known antioxidants (vitamin E) and in particular preferentially directed towards the radicalic species of oxygen.

On the basis of the experimental indications specified above, an object of the present invention therefore relates to the use of FPA and FPB in the preparation of pharmaceutical, or nutritional compositions, or compositions which can be used as food integrators, for administering to human beings, in which an antioxidant activity is required.

What is claimed is:

1. A compound having the formula (I)

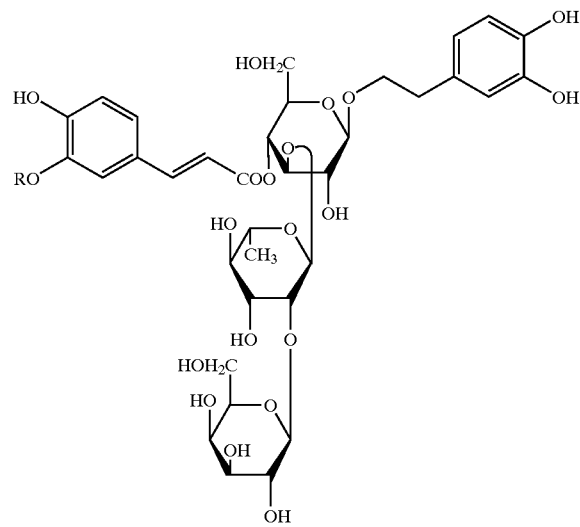

wherein R is CH$_3$.

2. A composition useful as food integrator comprising a compound having the formula (I)

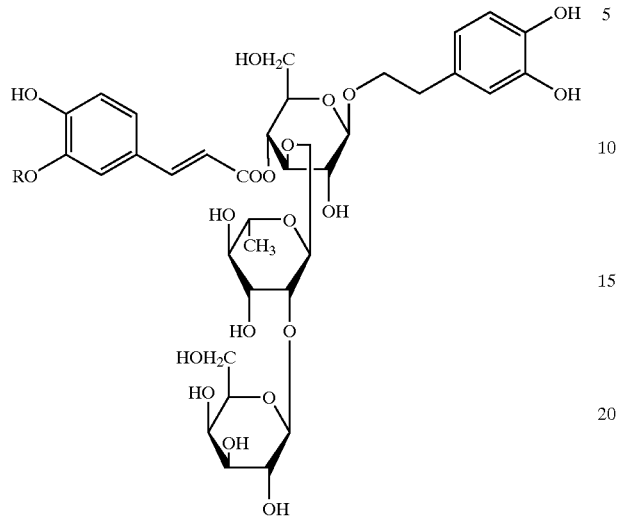

wherein R is CH$_3$.

3. A Pharmaceutical composition comprising a compound having the formula (I)

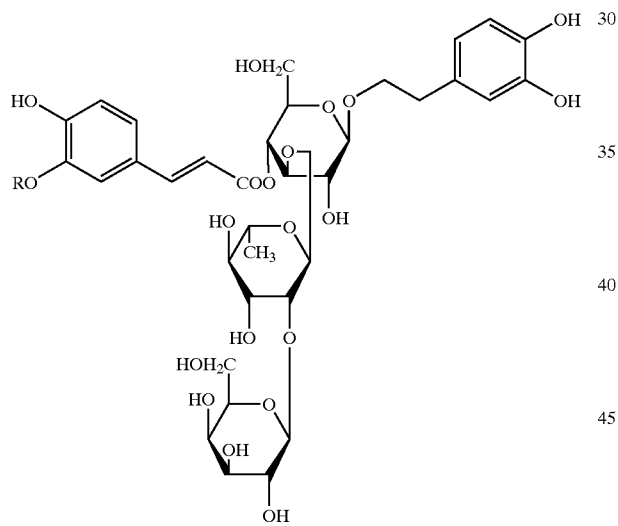

wherein R is CH$_3$;

in association with a pharmaceutically acceptable carrier.

4. A process or the preparation of a compound having the formula (I)

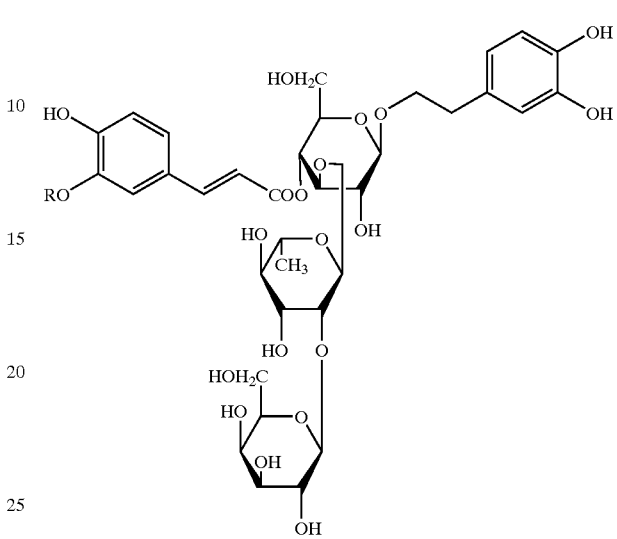

wherein R is H or CH$_3$, comprising obtaining a cellular culture from a plant of *Ajuga reptans* and subjecting said culture to cultivation under aerobic conditions in a liquid medium containing assimilable carbon, a nitrogen source and mineral salts.

5. The process according to claim 4, wherein said cultivation under aerobic conditions is carried out at a pH ranging from 5 to 7, at a temperature ranging from 18 to 32° C. and for a time ranging from 8 to 20 days.

* * * * *